United States Patent [19]

Taylor

[11] Patent Number: 5,344,932
[45] Date of Patent: Sep. 6, 1994

[54] N-(PYRROLO(2,3-D)PYRIMIDIN-3-YLACYL)-GLUTAMIC ACID DERIVATIVES

[75] Inventor: Edward C. Taylor, Princeton, N.J.

[73] Assignee: Trustees of Princeton University, Princeton, N.J.

[21] Appl. No.: 674,541

[22] Filed: Mar. 22, 1991

Related U.S. Application Data

[63] Continuation of Ser. No. 448,742, Dec. 11, 1989, abandoned, and Ser. No. 479,655, Feb. 8, 1990, abandoned.

[51] Int. Cl.$^5$ ............... C07D 487/04; A61K 31/505
[52] U.S. Cl. ........................................... 544/280
[58] Field of Search ................... 544/280; 514/258

[56] References Cited

U.S. PATENT DOCUMENTS

| 4,889,859 | 12/1989 | Taylor et al. | 514/258 |
| 4,996,206 | 2/1991 | Taylor et al. | 514/258 |
| 4,997,838 | 3/1991 | Akimoto et al. | 514/258 |

FOREIGN PATENT DOCUMENTS 334636  9/1989  European Pat. Off. .

*Primary Examiner*—Emily Bernhard
*Attorney, Agent, or Firm*—Mathews, Woodbridge & Collins

[57] ABSTRACT

N-(Acyl)glutamic acid derivatives in which the acyl group is substituted with 4-hydroxypyrrolo[2,3-d]pyrimidin-3-yl group are antineoplastic agents. A typical embodiment is N-[4-(2-{4-hydroxy-6-aminopyrrolo[2,3-d]pyrimidin-3-yl}ethyl)benzoyl]-L-glutamic acid.

7 Claims, No Drawings

N-(PYRROLO(2,3-D)PYRIMIDIN-3-YLACYL)-GLUTAMIC ACID DERIVATIVES

CROSS-REFERENCE TO RELATED APPLICATIONS

This is a continuation of Ser. No. 07/448,742 filed Dec. 11, 1989 and Ser. No. 07/479,655 filed Feb. 8, 1990 both now abandoned.

The present invention pertains to glutamic acid derivatives having the formula:

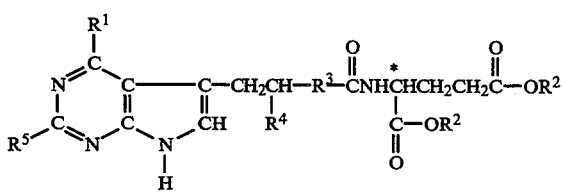

in which:
$R^1$ is —OH or —NH$_2$;
$R^2$ is hydrogen or a pharmaceutically acceptable cation;
$R^3$ is 1,4-phenylene or 1,3-phenylene unsubstituted or substituted with chloro, fluoro, methyl, methoxy, or trifluoromethyl; thienediyl or furanediyl each unsubstituted or substituted with chloro, fluoro, methyl, methoxy, or trifluoromethyl; cyclohexanediyl; or alkanediyl;
$R^4$ is hydrogen, methyl, or hydroxymethyl;
$R^5$ is hydrogen, alkyl of 1 to 6 carbon atoms, or amino; and
the configuration about the carbon atom designated * is S.

The compounds of this invention are herein described as embodying the pyrrolo[2,3-d]pyrimidine heterocyclic ring system which ring system is numbered as follows:

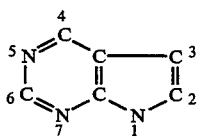

It will be appreciated that the pyrrolo[2,3-d]pyrimidines as depicted by Formula I are the tautomeric equivalent of the corresponding 5-H-6-oxo or 5-H-6-imino structures. Unless otherwise indicated, for simplicity's sake the compounds are depicted herein and named using the 6-hydroxy and 6-amino convention, it being understood the 5-H-6-oxo and 5-H-6-imino structures are fully equivalent.

The compounds of Formula I have an inhibitory effect on one or more enzymes which utilize folic acid, and in particular metabolic derivatives of folic acid, as a substrate. The compounds appear to be particularly active as inhibitors of thymidylate synthetase, which catalyses the methylation of deoxyuridylic acid to deoxythymidylic acid utilizing $N^5,N^{10}$-methylidenetetrahydrofolate as a coenzyme. The compounds thus can be used, alone or in combination, to inhibit the growth of those neoplasms which otherwise depend upon the inhibited enzyme.

The invention also pertains to the pharmaceutically acceptable salts of the compounds of Formula I, to processes for the preparation of these compounds and their salts, to chemical intermediates useful in preparation of these compounds, to a method of combatting neoplastic growth in a mammal, and to pharmaceutical compositions containing these compounds or their salts.

A first group of useful chemical intermediates, which can be converted directly to the desired final compounds of Formula I through removal of protecting groups, are compounds of the formula:

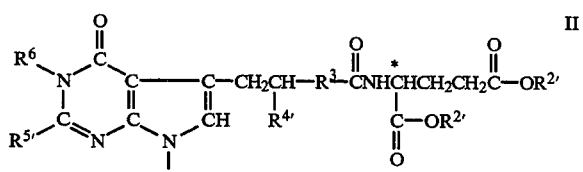

in which:
$R^3$ is as defined above;
$R^{2'}$ is hydrogen or a carboxy protecting group;
$R^{4'}$ is hydrogen, methyl, hydroxymethyl, or hydroxymethyl carrying a hydroxy protecting group;
$R^{5'}$ is hydrogen, alkyl, amino, or amino carrying a protecting group; and
$R^6$ is hydrogen or alkanoyoxy;
at least one of $R^{2'}, R^{4'}$, and $R^{5'}$ being a carboxy protecting group, a hydroxy protecting group, or an amino protecting group, respectively.

The compounds of Formula I can be employed in the form of the free dicarboxylic acid, in which case both $R^2$ groups are hydrogen. Alternatively, the compounds often can be employed advantageously in the form of a pharmaceutically acceptable salt, in which case one or both $R^2$ groups are a pharmaceutically acceptable cation. Such salt forms, including hydrates thereof, are often crystalline and advantageous for forming solutions or formulating pharmaceutical compositions. Pharmaceutically acceptable salts with bases include those formed from the alkali metals, alkaline earth metals, non-toxic metals, ammonium, and mono-, di- and trisubstituted amines, such as for example the sodium, potassium, lithium, calcium, magnesium, aluminum, zinc, ammonium, trimethylammonium, triethanolammonium, pyridinium, and substituted pyridinium salts. The mono and disodium salts, particularly the disodium salt, are advantageous.

The group $R^3$ is a divalent group having at least two carbon atoms between the carbon atoms carrying the free valence bonds. $R^3$ for example can be a 1,4-phenylene or 1,3-phenylene ring which is unsubstituted or optionally substituted with chloro, fluoro, methyl, methoxy, or trifluoromethyl.

Alternatively, $R^3$ can be a thienediyl or furanediyl group, that is, a thiophene or furane ring from which two hydrogen atoms have been removed from two ring carbon atoms, as for example the thiene-2,5-diyl, thiene-3,5-diyl, thiene-2,4-diyl, and thiene-3,4-diyl ring systems and the the furane-2,5-diyl, furane-3,5-diyl, furane-2,4-diyl, and furane-3,4-diyl ring systems, which ring systems can be unsubstituted or substituted with chloro, fluoro, methyl, methoxy, or trifluoromethyl. It will be appreciated that whereas in the abstract the thiene-3,5-diyl system is the equivalent of the thiene-2,4-diyl system, the two terms are utilized herein to denote the two isomeric forms resulting from the orientation of the thiophene ring within the remainder of the molecule:

e.g. the structure in which the depicted carboxy group adjacent to $R^3$ is in the 2-position of the thiophene ring and that in which the depicted carboxy group adjacent to $R^3$ is in the 3-position of the thiophene ring. The same conventionas apply to the furane ring.

Alternatively, $R^3$ can be a cyclohexanediyl group, namely a divalent cycloalkane group of 6 carbon atoms such as cyclohexane-1,3-diyl and cyclohexane-1,4-diyl.

Alternatively, $R^3$ can be a alkanediyl, namely a straight or branched divalent aliphatic group of from 2 to 4 carbon atoms such as ethano, trimethylene, tetramethylene, propane-1,2-diyl, propane-2,3-diyl, butane-2,3-diyl, butane-1,3-diyl, and butane-2,4-diyl. It again will be appreciated that whereas in the abstract propane-1,2-diyl is the equivalent of propane-2,3-diyl, and butane-1,3-diyl the equivalent of butane-2,4-diyl, the two terms are utilized herein to denote the two isomeric forms resulting from the orientation of an unsymmetrical alkanediyl chain with respect to the remainder of the molecule.

The protecting groups designated by $R^{2'}$, $R^{4'}$ and $R^{5'}$ and utilized herein denote groups which generally are not found in the final therapeutic compounds but which are intentionally introduced at a stage of the synthesis in order to protect groups which otherwise might react in the course of chemical manipulations, thereafter being removed at a later stage of the synthesis. Since compounds bearing such protecting groups thus are of importance primarily as chemical intermediates (although some derivatives also exhibit biological activity), their precise structure is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schröder and Lubke, Academic Press, London and New York, 1965; "Methoden der organischen Chemie", Houben-Weyl, 4th Edition, Vol.15/I, Georg Thieme Verlag, Stuttgart 1974, the disclosures of which are incorporated herein by reference.

With respect to $R^{2'}$, a carboxy group can be protected as an ester group which is selectively removable under sufficiently mild conditions not to disrupt the desired structure of the molecule, especially a lower alkyl ester of 1 to 12 carbon atoms such as methyl or ethyl and particularly one which is branched at the 1-position such as t.-butyl; and such lower alkyl ester substituted in the 1- or 2-position with (i) lower alkoxy, such as for example, methoxymethyl, 1-methoxyethyl, and ethoxymethyl, (ii) lower alkylthio, such as for example methylthiomethyl and 1-ethylthioethyl; (iii) halogen, such as 2,2,2-trichloroethyl, 2-bromoethyl, and 2-iodoethoxycarbonyl; (iv) one or two phenyl groups each of which can be unsubstituted or mono-, di- or tri-substituted with, for example lower alkyl such as tert.-butyl, lower alkoxy such as methoxy, hydroxy, halo such as chloro, and nitro, such as for example, benzyl, 4-nitrobenzyl, diphenylmethyl, di-(4-methoxyphenyl)methyl; or (v) aroyl, such as phenacyl. A carboxy group also can be protected in the form of an organic silyl group such as trimethylsilylethyl or tri-lower alkylsilyl, as for example trimethylsilyloxycarbonyl.

With respect to $R^{4'}$, a hydroxy group can be protected through the formation of acetals and ketals, as for example through formation of the tetrahydropyr-2-yloxy (THP) derivative.

With respect to $R^{5'}$, an amino group can be protected as an amide utilizing an acyl group which is selectively removable under mild conditions, especially formyl, a lower alkanoyl group which is branched α to the carbonyl group, particularly tertiary alkanoyl such as pivaloyl, or a lower alkanoyl group which is substituted in the position α to the carbonyl group, as for example trifluoroacetyl.

Preferred compounds of Formula I are those wherein $R^5$ is amino or hydrogen. Within this class, $R^1$ preferably is hydroxy, $R^3$ is 1,4-phenylene, and $R^4$ is hydrogen or hydroxymethyl. Also preferred within this class are the compounds in which $R^1$ is hydroxy, $R^3$ is thienediyl, and $R^4$ is hydrogen or hydroxymethyl.

The compounds of this invention can be prepared according to a first process through catalytic hydrogenation of a compound of the formula:

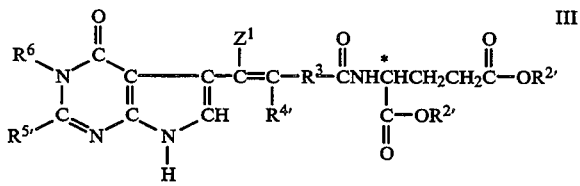

in which:
Z$^1$ is hydrogen, or Z$^1$ taken together with $R^{4'}$ is a carbon-carbon bond;
$R^{2'}$ is hydrogen or a carboxy protecting group;
$R^3$ and $R^6$ are as defined above;
$R^{4'}$, when taken independently of Z$^1$, is hydrogen, methyl, hydroxymethyl, or hydroxymethyl substituted with a hydroxy protecting group; and
$R^{5'}$ is hydrogen, alkyl of 1 to 6 carbon atoms, amino, or an amino protecting group.

Suitable hydrogenation catalysts include noble metals and noble metal oxides such as palladium or platinum oxide, rhodium oxide, and the foregoing on a support such as carbon or calcium oxide.

When in Formula III, Z$^1$ taken together with $R^{4'}$ is a carbon-carbon bond, that is, when a triple bond is present between the two carbon atoms to which Z$^1$ and $R^{4'}$ are bound, $R^{4'}$ in the hydrogenation product will be hydrogen. Absent any chirality in $R^3$ (or any protecting group encompassed by $R^{2'}$, $R^{4'}$ and/or $R^{5'}$), the hydrogenation product will be a single enantiomer having the S-configuration about the carbon atom designated *. This also is true when Z$^1$ and $R^{4'}$ are each hydrogen, that is, when a double bond is present between the two carbon atoms to which Z$^1$ and $R^{4'}$ are bound.

When, on the other hand, $R^{4'}$ is other than hydrogen, a mixture of the R,S and S,S diastereomers is obtained. The diastereomeric mixture can be used therapeutically as such (after removal of the protecting groups) or can be separated mechanically as by chromatography. Alternatively, the individual diastereomers can be separated chemically by forming salts with a chiral acid, such as the individual enantiomers of 10-camphorsulfonic acid, campboric acid, alphabromocamphoric acid, methoxyacetic acid, tartaric acid, diacetyltartaric acid, malic acid, pyrrolidone-5-carboxylic acid, and the like, and then freeing one or both of the individual diastereomeric bases, optionally repeating the process, so as obtain either or both substantially free of the other; i.e., in a form having an optical purity of >95%.

The protecting groups encompassed by $R^{2'}$, $R^{4'}$, $R^{5'}$, and/or $R^6$ can be removed following hydrogenation through acidic or basic hydrolysis, as for example with hydrogen chloride to cleave an $R^{4'}$ protecting group or with sodium hydroxide to cleave $R^{2'}$ or $R^{5'}$ protecting groups, thereby yielding the compounds of Formula I. Methods of removing the various protective groups are described in the standard references noted above and incorporated herein by reference.

Compounds of Formula III can be prepared utilizing procedures analogous to those described in U.S. Pat. No. 4,818,819, utilizing however the corresponding halogenated pyrrolo[2,3-d]pyrimidine. Thus a pyrrolo[2,3-d]pyrimidine of the formula:

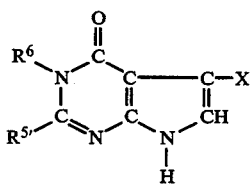

in which X is bromo or iodo, $R^{5'}$, and $R^6$ are as herein defined, is allowed to react with an unsaturated compound of the formula:

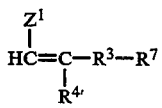

in which $Z^1$, $R^3$ and $R^{4'}$ are as herein defined, and $R^7$ is

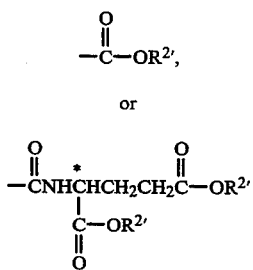

in which $R^{2'}$ is as herein defined, in the presence of a palladium/trisubstituted phosphine catalyst of the type described in U.S. Pat. No. 4,818,819, the disclosure of which is incorporated herein by reference.

When $R^7$ is —CONHCH(COOR$^{2'}$)CH$_2$CH$_2$COOR$^{2'}$, the product of this coupling reaction is hydrogenated, and any protecting group removed, as described above.

Alternatively, a compound of Formula IV is allowed to react with a compound of the formula:

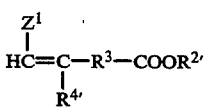

in which $Z^1$, $R^{2'}$, $R^3$, and $R^{4'}$ are as herein defined in the presence of a palladium/trisubstituted phosphine catalyst of the type described in U.S. Pat. No. 4,818,819 to yield an intermediate of the formula:

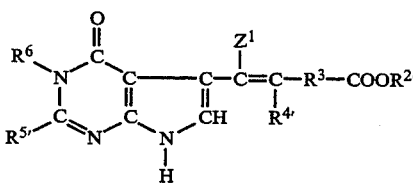

The product of Formula VII then can be hydrogenated, hydrolysed to remove the $R^{2'}$ and $R^6$ protecting groups, and, optionally with intermediate protection of any amino group encompassed by $R^{5'}$, and coupled with a protected glutamic acid derivative in the manner described in U.S. Pat. No. 4,684,653 using conventional condensation techniques for forming peptide bonds such as DCC or diphenylchlorophosphonate, following which the protecting groups are removed.

In a further variant, compounds of Formula III can be prepared utilizing the procedures described in U.S. Pat. No. 4,818,819. Thus a compound of the formula:

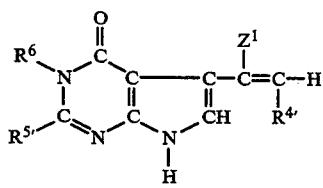

in which $Z^1$, $R^{4'}$, $R^{5'}$, and $R^6$ are as herein defined, is allowed to react with a compound of the formula:

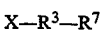

in which X, $R^3$, and $R^7$ are as herein defined, in the presence of a palladium/trisubstituted phosphine catalyst of the type described in U.S. Pat. No. 4,818,819. This variant of the process is particularly suitable for, but is not limited to, preparation of those compounds in which $R^4$ is hydroxymethyl, in which case $R^{4'}$ in Formula VI is a protected hydroxymethyl group, as for example tetrahydropyran-2-yloxymethyl.

Compounds of Formula VIII also can be obtained by the methods of U.S. Pat. No. 4,818,819 by treating a compound of Formula IV with an unsaturated compound of the formula:

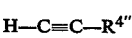

in which $R^{4''}$ is methyl, a protected hydroxymethyl, or a trisubstituted silyl group in the presence of a palladium/trisubstituted phosphine catalyst of the type discussed above. This procedure is particularly suitable for, but is not limited to, preparation of those compounds in which $R^4$ is hydroxymethyl.

Although not always the case, the compounds of Formula IV in which $R^6$ is hydrogen can tend to be somewhat insoluble in solvents suitable for the reaction described in U.S. Pat. No. 4,818,819. In such instances, the compounds of Formula IV in which $R^6$ is hydrogen can be first treated with with sodium hydride and a suitable alkyl alkanoate (such as chloromethyl pivalate) to introduce an alkanoyloxy group in the 5-position and increase solubility.

A useful subclass of compounds useful both as intermediates and for their effect on enzymes are derivatives of Formula XI and XII lacking the glutamic acid sidechain:

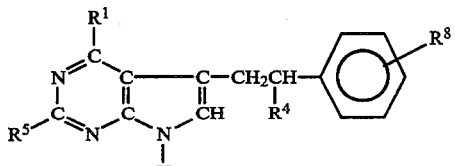

and

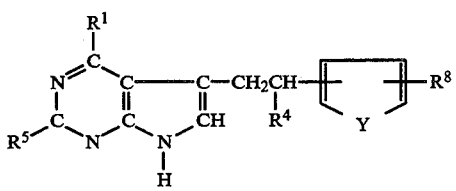

in which:
R¹ is —OH or —NH₂;
R⁴ is hydrogen, methyl, or hydroxymethyl;
R⁵ is hydrogen, alkyl of 1 to 6 carbon atoms, or amino;
R⁸ is hydrogen, chloro, fluoro, methyl, methoxy, trifluoromethyl, or carboxy; and
Y is —S— or —O—; and
the pharmaceutically acceptable salts thereof.

Compounds of Formulas XI and XII are obtained by allowing a compound of Formula VII to react with a compound of the formula:

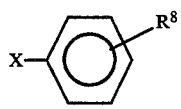

or

in which X, Y, and R⁸ are as herein defined, by the methods of U.S. Pat. No. 4,818,819, namely in the presence of a palladium/trisubstituted phosphine catalyst, with the resulting coupled product being hydrogenated and hydrolysed to remove the R²′ protecting group. Typical compounds of Formulas XI and XII are 3-(2-phenylethyl)-4-hydroxy-6-aminopyrrolo[2,3-d]pyrimidine, 3-[2-(3-fluorophenyl)ethyl]-4-hydroxy-6-aminopyrrolo[2,3-d]pyrimidine, 3-[2-(4-fluorophenyl)ethyl]-4-hydroxy-6-aminopyrrolo[2,3-d]pyrimidine, 3-[2-(4-carboxyphenyl)ethyl]-4-hydroxy-6-aminopyrrolo[2,3-d]-pyrimidine, 3-[2-(4-methoxyphenyl)ethyl]-4-hydroxy-6-aminopyrrolo[2,3-d]pyrimidine, 3-[2-(4-methylphenyl)ethyl]-4-hydroxy-6-aminopyrrolo[2,3-d]pyrimidine, 3-(2-phenylethyl)-4-hydroxypyrrolo[2,3-d]pyrimidine, 3-(2-phenylethyl)-4-hydroxy-6-methylpyrrolo[2,3-d]pyrimidine, 3-(2-phenyl-3-hydroxypropyl)-4-hydroxy-6-aminopyrrolo[2,3-d]pyrimidine, 3-[2-(thien-2-yl)ethyl]-4-hydroxy-6-aminopyrrolo[2,3-d]pyrimidine, 3-[2-(thien-2-yl)ethyl]-4-hydroxypyrrolo[2,3-d]pyrimidine, 3-[2 -(thien-2-yl)ethyl]-4-hydroxy-6-methylpyrrolo[2,3-d]-pyrimidine, 3-[2-(thien-3-yl)ethyl]-4-hydroxy-6-aminopyrrolo[2,3-d]pyrimi- dine, 3-[2-(thien-3-yl)ethyl]-4-hydroxypyrrolo[2,3-d]pyrimidine, 3-[2-(thien-3-yl)ethyl]-4-hydroxy-6-methylpyrrolo[2,3-d]pyrimidine, 3-[2-(fur-2-yl)ethyl]-4-hydroxy-6-aminopyrrolo[2,3-d]pyrimidine, 3-[2-(fur-2-yl)ethyl]-4-hydroxypyrrolo[2,3-d]pyrimidine, 3-[2-(fur-2-yl)ethyl]-4-hydroxy-6-methylpyrrolo[2,3-d]pyrimidine, 3-[2-(fur-3-yl)ethyl]-4-hydroxy-6-aminopyrrolo[2,3-d]pyrimidine, 3-[2-(fur-3-yl)ethyl]-4-hydroxypyrrolo[2,3-d]pyrimidine, and 3-[2-(fur-3-yl)ethyl]-4-hydroxy-6-methylpyrrolo[2,3-d]pyrimidine.

As discussed above, the compounds of this invention can be prepared utilizing the palladium catalyzed coupling of various unsaturated compounds described in U.S. Pat. No. 4,818,819 and the glutamic acid coupling reactions described in U.S. Pat. No. 4,684,653, substituting the appropriate pyrrolo[2,3-d]pyrimidine for the pyrido[2,3-d]pyrimidine therein disclosed. The pyrrolo[2,3-d]pyrimidine intermediates of Formula IV above can be obtained by treating a compound of the formula:

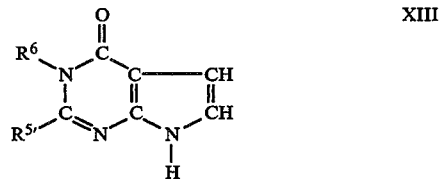

in which R⁵′ and R⁶ are as herein defined with N-iodosuccinimide to yield the corresponding 2,3-diiodopyrrolo[2,3-d]pyrimidine which then is treated with zinc and acetic acid to remove selectively the iodine atom in the 2-position, yielding the corresponding 3-iodopyrrolo[2,3-d]pyrimidine of Formula IV.

According to the foregoing processes, compounds of Formula II in which R¹ is —OH are obtained. When a compound of Formula I in which R¹ is —NH₂ is desired, a compound in which R¹ is —OH can be treated with 1,2,4-triazole and (4-chlorophenyl)dichlorophosphate and the product of this reaction then treated with concentrated ammonia.

As noted, the compounds of this invention have an effect on one or more enzymes which utilize folic acid, and in particular metabolic derivatives of folic acid, as a substrate. For example, N-(4-[2-(4-hydroxy-6-aminopyrrolo[2,3-d]pyrimidin-3-yl)ethyl]benzoyl)-L-glutamic acid demonstrates potent inhibitory effects against growth of human T-cell derived lyphoblastic leukemia cells (CCRF-CEM), exhibiting an IC₅₀ of 0.004 μ/ml. Cytotoxicity is not reversed by addition of purines such as hypoxanthine or by addition of aminoimidazolecarboxamide but is reversed by addition of thymidine, indicating specific inhibition in the tymidylate cycle and not in de novo purine synthesis. The compounds can be used, under the supervision of qualified professionals, to inhibit the growth of neoplasms including choriocarcinoma, leukemia, adenocarcinoma of the female breast, epidermid cancers of the head and neck, squamous or small-cell lung cancer, and various lymphosarcomas. The compounds can also be used to treat mycosis fungoides and psoriasis.

The compounds can be administered orally but preferably are administered parenterally, alone or in combination with other therapeutic agents including other anti-neoplastic agents, steroids, etc., to a mammal suffering from neoplasm and in need of treatment. Parenteral routes of administration include intramuscular, intrathecal, intravenous and intra-arterial. Dosage regimens must be titrated to the particular neoplasm, the condition of the patient, and the response but generally doses will be from about 10 to about 100 mg/day for 5-10 days or single daily administration of 250-500 mg, repeated periodically; e.g. every 14 days. While having a low toxicity as compared to other antimetabolites now in use, a toxic response often can be eliminated by either or both of reducing the daily dosage or administering the compound on alternative days or at longer intervals such as every three days. Oral dosage forms include tablets and capsules containing from 1-10 mg of drug per unit dosage. Isotonic saline solutions containing 20-100 mg/ml can be used for parenteral administration.

The following examples will serve to further illustrate the invention. In the NMR data, "s" denotes singlet, "d" denotes doublet, "t" denotes triplet, "q" denotes quartet, "m" denotes multiplet, and "br" denotes a broad peak.

EXAMPLE 1

3-Iodo-4-hydroxy-6-Pivaloylaminopyrrolo[2,3-d]pyrimidine

A mixture of 3.0 g (0.02 mole) of 4-hydroxy-6-aminopyrrolo[2,3-d]pyrimidine and 8.4 g (0.07 mol) of pivaloyl chloride in 40 mL of pyridine is stirred for 30 minutes at from 80° to 90° C., the mixture then evaporated to dryness, and the residue dissolved in 30 mL of methanol. Addition of 10% aqueous ammonia yields 4.2 g (89%) of 4-hydroxy-6-pivaloylaminopyrrolo[2,3-d]pyrimidine which can be further purified by chromatography through silica gel, eluting with 8% methanol in methylene chloride. mp 295° C. $^1$NMR (d$_6$-DMSO)$\delta$1.20(s, 9H), 6.37 (d, J=3.4 Hz, 1H), 6.92 (d, J=3.4 Hz, 1H), 10.78 (s, 1H), 11.56 (s, 1H), 11.82 (s, 1H). Anal. Calc. for $C_{11}H_{14}N_4O_2$: C, 56.40; H, 6.02; N, 23.92. Found: C, 56.16; H, 6.01; N, 23.67.

To a mixture of 4.7 g (20 mmol) of 4-hydroxy-6-pivaloylaminopyrrolo[2,3-d]pyrimidine in 200 mL of dimethylformamide are added 9.9 g (44 mmol) of N-iodosuccinamide. The mixture is stirred at ambient temperature in the dark for 18 hours. Most of the dimethylformamide is removed by evaporation and the residual slurry poured into 300 mL of water. The resulting solid is collected by filtration and dried under vacuum over phosphorus pentoxide to yield 2,3-diiodo-4-hydroxy-6-pivaloylaminopyrrolo[2,3-d]pyrimidine which can be purified further by chromatography over silica eluting with 2.5% methanol in methylene chloride. mp >290° C. $^1$NMR (d$_6$-DMSO)$\delta$1.18(s, 9H), 10.85 (s, 1H), 11.85 (s, 1H), 12.42 (s, 1H). Anal. Calc. for $C_{11}H_{12}N_4O_2I_2$: C, 27.18; H 2.49; N, 11.53; I, 52.22. Found: C, 27.51; H, 2.51; N, 11.27;I, 52.02.

In a similar fashion but starting with 4-hydroxy-6-methylpyrrolo[2,3-d]pyrimidine and 4-hydroxypyrrolo[2,3-d]pyrimidine (7-deazahypoxanthine) there are respectively obtained 2,3-diiodo-4-hydroxy-6-methylpyrrolo[2,3-d]pyrimidine, mp 233° C., and 2,3-diiodo-4-hydroxypyrrolo[2,3-d]pyrimidine, mp >205° C. (compound loses iodine). $^1$NMR (d$_6$-DMSO)$\delta$7.79 (s, 1H), 11.93 (s, 1H), 12.74 (s, 1H).

To a mixture of 4.86 g of 2,3-diiodo-4-hydroxy-6-pivaloylaminopyrrolo[2,3-d]pyrimidine in 100 mL of glacial acetic acid and 25 mL of water are added 1.3 g (20 mmol) of zinc powder. The mixture is stirred at ambient temperature for 18 hours, diluted with 500 mL of water, and cooled. The solid is collected through filtration and dried under vacuum over phosphorus pentoxide to yield 3-iodo-4-hydroxy-6-pivaloylaminopyrrolo[2,3-d]pyrimidine which can be purified further by chromatography over silica eluting with 2.5% methanol in methylene chloride. mp >240° C. $^1$NMR (d$_6$-DMSO)$\delta$1.20(s, 9H), 7.12 (d, J=1.8 Hz, 1 H), 10.82 (s, 1H), 11.79 (s, 1H), 11.89 (s, 1H). Anal. Calc. for $C_{11}H_{13}N_4O_2I$: C, 36.69; H 3.64; N, 15.56; I, 35.24. Found: C, 36.91; H, 3.58; N, 15.65; I, 35.56.

In a similar fashion from 2,3-diiodo-4-hydroxy-6-methylpyrrolo[2,3-d]pyrimidine and 2,3-diiodo-4-hydroxypyrrolo[2,3-d]pyrimidine, there are respectively obtained 3-iodo-4-hydroxy-6-methylpyrrolo[2,3-d]pyrimidine m.p 245° C., and 3-iodo-4-hydroxypyrrolo[2,3-d]pyrimidine, mp >245° C. (compound loses iodine). $^1$NMR (d$_6$-DMSO)$\delta$7.20 (d, J=2.2 Hz, 1H), 7.82 (d, J=2.8 Hz, 1H), 11.85 (d, J=1.1 Hz, 1H), 12.17 (s, 1H).

EXAMPLE 2

Dimethyl N-[4-(4-hydroxy-6-pivaloylaminopyrrolo[2,3-d]pyrimidin-3-ylethynyl)benzoyl]-L-glutamate To a mixture of 3.6 g (10 mmol) of well-dried 3-iodo-4-hydroxy-6-pivaloylaminopyrrolo[2,3-d]pyrimidine in 40 mL of dimethylformamide are added 4.0 g (13.19 mmol) of dimethyl N-(4-ethynylbenzoyl)-L-glutamate, 0.38 g of copper (I) iodide, 3 mL of triethylamine, and 1.0 g of tetrakis-(triphenylphosphine)palladium. This mixture is stirred at ambient temperatures for two hours and then poured into 500 mL of water. The solid is collected by filtration, air dried, and then refluxed in 200 mL of methanol. The mixture is cooled and the solid collected by filtration, dissolved in two liters of 10% methanol in methylene chloride, and chromatographed over silica. Initial black bands are rechromatographed and the combined colorless bands from the first and second runs are evaporated to give 3.5 g of dimethyl N-[4-(4-hydroxy-6-pivaloylaminopyrrolo[2,3-d]pyrimidin-3-ylethynyl)benzoyl]-L-glutamate which can be purified further by recrystallization from 50% methanol in methylene chloride. mp 280°-285° C. $^1$NMR (d$_6$-DMSO)$\delta$1.21 (s, 9H), 1.96-2.15 (m, 2H), 2.44 (t, J=7.5 Hz, 2H) 3.56 (s, 3H), 3.62 (s, 3H), 4.40-4.45 (m, 1H), 7.43 (s, 1H), 7.53 (d, J=8.4 Hz, 2 H), 7.87 (d, J=8.4 Hz, 2 H), 8.82 (d, J=7.4 Hz, 1 H), 10.95 (s, 1H), 11.95 (s, 1H). Anal. Calc. for $C_{27}H_{29}N_5O_7$: C, 60.56; H 5.46; N, 13.08. Found: C, 60.55; H, 5.46; N, 12.89.

In a similar fashion by substituting an equivalent amount of dimethyl N-(pent-4-ynoyl)-L-glutamate, dimethyl N-(hept-6-enoyl)-L-glutamate, and dimethyl N-(hex-5-ynoyl)-L-glutamate for dimethyl N-(4-ethynylbenzoyl)glutamate in the foregoing procedure, there are obtained dimethyl N-[5-(4-hydroxy-6-pivaloylaminopyrrolo[2,3-d]pyrimidin-3-yl)pent-4-ynoyl]-L-glutamate, dimethyl N-[7-(4-hydroxy-6-pivaloylaminopyrrolo[2,3-d]-pyrimidin-3-yl)hept-6-enoyl]-L-glutamate, and dimethyl N-[6-(4-hydroxy-6-pivaloylaminopyrrolo[2,3-d]pyrimidin-3-yl)hex-5-ynoyl]-L-glutamate.

Dimethyl N-(hex-5-ynoyl)-L-glutamate can be obtained in the manner described generally in U.S. Pat. No. 4,882,334 issued Nov. 21, 1989, the disclosure of which is incorporated herein by reference, by allowing hex-5-ynoic acid chloride (obtained by treating hex-5-ynoic acid with thionyl chloride) to react with dimethyl L-glutamate in the presence of an acid acceptor such as triethylamine. Hex-5-ynoic acid in turn can be prepared, for example, by alkaline hydrolysis of 5-cyanopent-1-yne.

EXAMPLE 3

Diethyl N-[4-{1-hydroxy-3-(4-hydroxy-06-aminopyrrolo[2,3-d]pyrimidin-3-yl)prop-2-yl}benzoyl]glutamate A mixture of 14.6 g of 3-iodo-4-hydroxy-6-pivaloylaminopyrrolo[2,3-d]pyrimidine, 7.6 g of 2-(2-propynyloxy)-tetrahydropyran, 798 mg (10%) of palladium chloride, 2.36 g (20%) of triphenyl phosphine, 428 mg (5%) of cuprous iodide, 45 ml of triethyl amine and 700 ml of acetonitrile is heated at reflux under nitrogen for 12 hours. There then are added to the hot reaction mixture 3.2 g of 2-(2-propynyloxy)-tetrahydropyran and reflux is continued for an additional 12 hours. After heating for a total of 24 hours under reflux, the solvent is removed under reduced pressure, and the residue filtered through silica gel using 2% methanol in methylene chloride. This filtrate is concentrated and chromatographed on silica gel eluting with 20:1 ethyl acetate:hexane mixture to give 3-(3-tetrahydropyr-2-yloxy-prop-1-yn-1-yl)-4-hydroxy-6-pivaloylaminopyrrolo[2,3-d]pyrimidine which is further purified by recrystallization with ethyl acetate.

A mixture of 2 g of 3-(3-tetrahydropyr-2-yloxyprop-1-yn-1-yl)-4-hydroxy-6-pivaloylaminopyrrolo[2,3-d]pyrimidine, 40 ml of methanol, 20 ml of chloroform, 40 mg of 5% palladium on barium sulfate, and 40 mg of synthetic quinoline is stirred under 1 atmosphere hydrogen pressure for 40 min. The solvent then is removed by evaporation and the residue diluted with methylene chloride. The methylene chloride solution is filtered through silica gel with 2% methanol in methylene chloride to remove catalyst and the filtrate then concentrated to give an oil which upon adding ether yields 3-(3-tetrahydropyr-2-yloxyprop-1-en-1-yl)-4-hydroxy-6-pivaloylaminopyrrolo[2,3-d]pyrimidine which can be further purified through column chromatography eluting with ethyl acetate and recrystallization using ethyl acetate.

A mixture containing 3.48 g of 3-(3-tetrahydropyr-2-yloxyprop-1-en-1-yl)-4-hydroxy-6-pivaloylaminopyrrolo[2,3-d]pyrimidine, 3.12g (1.2 equiv.) of diethyl N-(4-iodobenzoyl)glutamate, 546 mg (20%) of tris-(2-methylphenyl)phosphine, 201 mg (10%) of palladium acetate and 85.5 mg (5%) of cuprous iodide in 15 ml of triethylamine and 240 ml of acetonitrile is heated at reflux under nitrogen. After 12 hours., 1.17 g of diethyl N-(4-iodobenzoyl)glutamate are added and the reaction mixture is heated at reflux under nitrogen for an additional 12 hours. The reaction mixture then is concentrated under reduced pressure and the residue chromatographed on silica gel, eluting with 20:1 ethyl acetate:-hexane. (Any recovered starting material can be recycled through the foregoing procedure.) The concentrated material is dissolved in 1:5 ethyl acetate:ether and this solution is refrigerated for 15 hours. The solid which forms is collected by filtration, washed with cold ethyl acetate and dried to yield diethyl N-[4-(1-(tetrahydropyr-2-yloxy)-3-(4-hydroxy-6 -pivaloylaminopyrrolo[2,3-d]pyrimidin-3-yl)prop-2-en-2yl)benzoyl]glutamate.

EXAMPLE 4

Dimethyl N-[5-(4-hydroxy-6-pivaloylaminopyrrolo[2,3-d]pyrimidin-3-yl}ethynyl)thien-2-ylcarbonyl]-L-glutamate A mixture of 2.0 g of 3-iodo-4-hydroxy-6-pivaloylaminopyrrolo[2,3-d]pyrimidine, 1.2 g. of trimethylsilylacetylene, 0.1 g of palladium chloride, 0.23 g of triphenylphosphine, 0.06 g of cuprous iodide, and 2.6 g of triethylamine in 100 mL of acetonitrile is heated in a sealed tube for 1.5 hours at 50° C. and then at reflux for 3 hours. The solvent is removed under reduced pressure and the residue triturated with 1:1 ethyl acetate:hexanes and filtered. The solid thus collected is dissolved in methylene chloride and this solution is passed through a pad of silica gel eluting with 1% methanol on methylene chloride. The eluate is concentrated to yield 3-trimethylsilylethynyl-4-hydroxy-6-pivaloylaminopyrrolo[2,3-d]pyrimidine.

To a solution of 1.5 g of 3-trimethylsilylethynyl-4-hydroxy-6-pivaloylaminopyrrolo[2,3-d]pyrimidine in 100 mL of anhydrous tetrahydrofuran cooled to 0° C. are added under nitrogen 4.75 mL of 1M tetrabutylammonium fluoride in anhydrous tetrahydrofuran. After 5 minutes, the reaction mixture is allowed to attain room temperature and is then stirred for 2 hours. The solvent is removed under reduced pressure and the residue is purified by chromatography over silica gel to yield 3-ethynyl-4-hydroxy-6-pivaloylaminopyrrolo[2,3-d]pyrimidine.

A mixture of 1.70 g. of 3-ethynyl-4-hydroxy-6-pivaloylaminopyrrolo[2,3-d]pyrimidine, 2.30 g. of dimethyl N-(5-bromothien-2-ylcarbonyl)-L-glutamate (prepared as described in U.S. Pat. No. 4,882,333 issued Nov. 21, 1989, the disclosure of which is incorporated herein by reference), 44 mg. of palladium chloride, 130 mg. of triphenylphosphine, 25 mg. of cuprous iodide, and 1.13 mL. of triethylamine in 30 mL. of acetonitrile is heated at reflux for 3 hours and then cooled to ambient temperature. The solvent is removed under reduced pressure and the residue column chromatographed (Waters 500) eluting with 1:19 methanol:methylene chloride to yield dimethyl N-[5-(4-hydroxy-6-pivaloylaminopyrrolo[2,3-d]pyrimidin-3-yl)ethynyl)thien-2-ylcarbonyl]-L-glutamate.

By substituting equivalent amounts of diethyl N-(4-bromothien-2-ylcarbony)-L-glutamate, and diethyl N-(5-bromothien-3-ylcarbony)-L-glutamate in the foregoing procedure, there are respectively obtained diethyl N-[4-(4-hydroxy-6-pivaloylaminopyrrolo[2,3-d]pyrimidin-3-ylethynyl)thien-2-ylcarbonyl]-L-glutamate and diethyl N-[5-(4-hydroxy-6-pivaloylaminopyrrolo[2,3-d]pyrimidin3-ylethynyl)thien-3-ylcarbonyl]-L-glutamate.

Diethyl N-[4-(4-hydroxy-6-pivaloylaminopyrrolo[2,3-d]pyrimidin-3-ylethynyl)fur-2-ylcarbonyl]-L-glutamate and diethyl N-[5-(4-hydroxy-6-pivaloylaminopyrrolo[2,3-d]pyrimidin-3-ylethynyl)fur-3-ylcarbonyl]-L-glutamate can be similarly obtained from diethyl N(4-bromofur-2-ylcarbony)-L-glutamate and diethyl N-(5-bromofur-3-ylcarbony)-L-glutamate, respectively.

Similarly from dimethyl N-(2-fluoro-4-iodobenzoyl)-L-glutamate and dimethyl N-(3-fluoro-4-iodobenzoyl)-L-glutamate (prepared as described in U.S. Pat. No. 4,889,859 issued Dec. 26, 1989, the disclosure of which is incorporated herein by reference), there are respectively obtained dimethyl N-[2-fluoro-4-(4-hydroxy-6-pivaloylaminopyrrolo[2,3-d]pyrimidin-3-ylethynyl)benzoyl]-L-glutamate and dimethyl N-[3-fluoro-4-(4-hydroxy-6-pivaloylaminopyrrolo[2,3-d]pyrimidin-3-ylethynyl)benzoyl]-L-glutamate.

EXAMPLE 5

Dimethyl N-[4-(4-hydroxypyrrolo[2,3-d]pyrimidin-3-ylethynyl)-benzoyl]-L-glutamate By allowing 3-iodo-4-hydroxypyrrolo[2,3-d]pyrimidine to react with dimethyl N-(4-ethynylbenzoyl)-L-glutamate in the manner described in Example 2, there is obtained dimethyl N-[4-(4-hydroxypyrrolo[2,3-d]pyrimidin-3-ylethynyl)benzoyl]-L-glutamate which is purified by chromatography over silica, m.p. 160 ° C. (dec.). $^1$NMR (d$_6$-DMSO)δ1.98–2.15 (m, 2H), 2.45 (t, J=7.5 Hz, 2H) 3.57 (s, 3H), 3.64 (s, 3H), 4.40–4.45 (m, 1H), 7.51 ((d, J=2.5 Hz, 1H), 7.55 (d, J=8.2 Hz, 2 H), 7.87 (s, 1H), 7.90 (d, J=8.2 Hz, 1 H), 11.97 ((d, J=3.7 Hz, 1 H), 12.31 (s, 1H).

Alternatively, by substituting equivalent amounts of methyl 4-ethynylbenzoate, 4-ethynyltoluene, 4-ethynylbenzene, 4-ethynylchlorobenzene, 4-ethynylfluorobenzene, 3-ethynylfluorobenzene, and 1-methoxy-4ethynylbenzene in the procedure of Example 2, there are obtained methyl 4-(4-hydroxy-6-pivaloylaminopyrrolo[2,3-d]pyrimidin-3-ylethynyl)benzoate, 3-(4-methylphenyl)ethynyl-4-hydroxy-6-pivaloylaminopyrrolo[2,3-d]pyrimidine, 3-phenylethynyl-4-hydroxy-6-pivaloylaminopyrrolo[2,3-d]pyrimidine, 3-(4-chlorophenyl)ethynyl-4-hydroxy-6-pivaloylaminopyrrolo[2,3-d]pyrimidine, 3-(4 -fluorophenyl)ethynyl-4-hydroxy-6-pivaloylaminopyrrolo[2,3-d]pyrimidine, 3-(3-fluorophenyl)ethynyl-4-hydroxy-6-pivaloylaminopyrrolo[2,3-d]pyrimidine, and 3-(4-methoxyphenyl)ethynyl-4-hydroxy-6-pivaloylaminopyrrolo[2,3-d]pyrimidine.

Use of 3-iodo-4-hydroxypyrrolo[2,3-d]pyrimidine in place of 3-iodo-4-hydroxy-6-pivaloylaminopyrrolo[2,3-d]pyrimidine with methyl 4-ethynylbenzoate, 4-ethynyltoluene, 4-ethynylbenzene, 4-ethynylchlorobenzene, 4-ethynylfluorobenzene, 3-ethynylfluorobenzene, and 1-methoxy-4-ethynylbenzene yields respectively methyl 4-(4-hydroxypyrrolo[2,3-d]pyrimidin-3-ylethynyl)benzoate, 3-(4-methylphenyl)ethynyl-4-hydroxypyrrolo[2,3-d]pyrimidine, 3-phenylethynyl-4-hydroxypyrrolo[2,3-d]pyrimidine, 3-(4-chlorophenyl)ethynyl-4-hydroxypyrrolo[2,3-d]pyrimidine, 3-(4-fluorophenyl)ethynyl-4-hydroxypyrrolo[2,3-d]pyrimidine, and 3-(4-methoxyphenyl)ethynyl4-hydroxypyrrolo[2,3-d]pyrimidine.

Ten grams of 3-iodo-4-hydroxy-6-methylpyrrolo[2,3-d]pyrimidine are allowed to react with 2.19 g of 80% sodium hydride oil dispersion and 75 ml of dimethylformamide with the exclusion of moisture. After 30 minutes, 6.02 g of chloromethyl pivalate are added. This mixture is stirred for three hours poured into water, and neutralized with acetic acid. The solid is chromatographed on silica gel with acetone-dichloromethane to yield 3-iodo-4-hydroxy-1,5-bis-(pivaloyloxy)-6-methylpyrrolo[2,3-d]pyrimidine, m.p. 155° C. initially, followed by 3-iodo-4-hydroxy-5-pivaloyloxy-6-methylpyrrolo[2,3-d]pyrimidine, m.p. 236° C.

Use of 3-iodo-4-hydroxy-5-pivaloyloxy-6-methylpyrrolo[2,3-d]pyrimidine in the procedure of Example 2 then yields dimethyl N-[4-(4-hydroxy-5-pivaloyloxy-6-methylpyrrolo[2,3-d]pyrimidin-3-ylethynyl)benzoyl]-L-glutamate, m.p. 196° C. Anal. Calc. for C$_{29}$H$_{32}$N$_4$O$_8$: C, 61.70; H 5.71; N, 9.92. Found: C, 61.90; H, 5.71; N, 9.95.

Use of 3-iodo-4-hydroxy-5-pivaloyloxy-6-methylpyrrolo[2,3-d]pyrimidine in place of 3-iodo-4-hydroxy-6-pivaloylaminopyrrolo[2,3-d]pyrimidine with methyl 4-ethynylbenzoate, 4-ethynyltoluene, 4-ethynylbenzene, 4-ethynylchlorobenzene, 4-ethynylfluorobenzene, 3-ethynylfluorobenzene, and 1-methoxy-4-ethynylbenzene yields methyl 4-(4-hydroxy-5-pivaloyloxy-6-methylpyrrolo[2,3-d]pyrimidin-3-ylethynyl)benzoate, 3-(4-methylphenyl)ethynyl-4-hydroxy-5-pivaloyloxy-6-methylpyrrolo[2,3-d]-pyrimidine, 3-phenylethynyl-4-hydroxy-5-pivaloyloxy-6-methylpyrrolo[2,3-d]pyrimidine, 3-(4-chlorophenyl)ethynyl-4-hydroxy-5-pivaloyloxy-6-methylpyrrolo[2,3-d]pyrimidine, 3-(4-fluorophenyl)ethynyl-4-hydroxy-5-pivaloyloxy-6-methylpyrrolo[2,3-d]pyrimidine, and 3-(4-methoxyphenyl)ethynyl-4-hydroxy-5-pivaloyloxy-6-methylpyrrolo[2,3-d]pyrimidine.

EXAMPLE 6

Dimethyl N-{4-[2-(4-hydroxy-6-pivaloylaminopyrrolo[2,3-d]pyrimidin-3-yl)ethyl]benzoyl}-L-glutamate A mixture of 1.0 g of dimethyl N-[4-(4-hydroxy-6-pivaloylaminopyrrolo[2,3-d]pyrimidin-3-ylethynyl)benzoyl]-L-glutamate in 250 mL of 50% methanol in methylene chloride and 0.8 g of 3% palladium-on-carbon is hydrogenated at 50 p.s.i. for three hours, filtered, and concentrated under reduced pressure. The solid is collected by filtration and dried to yield 0.72 g of dimethyl N-{4-[2-(4-hydroxy-6-pivaloylaminopyrrolo[2,3-d]pyrimidin-3-yl)ethyl]benzoyl}-L-glutamate- mp 247° C. $^1$NMR (d$_6$-DMSO)δ1.21 (s, 9H), 1.90–2.12 (m, 2H), 2.42 (t, J=7.4 Hz, 2H), 2.92 (t, J=4 Hz, 2H), 2.97 (t, J=4 Hz, 2H), 3.55 (s, 3H), 3.61 (s, 3H), 4.38–4.45 (m, 1H), 6.61 (s, 1H), 7.27 (d, J=8.2 Hz, 2 H), 7.75 (d, J=8.2 Hz, 2 H), 8.64 (d, J=7.4 Hz, 1 H), 10.75 (s, 1H), 11.22 (s, 1H) . Anal. Calc. for C$_{27}$H$_{33}$N$_5$O$_7$: C, 60.10; H 6.17; N, 12 . 98. Found: C, 59.94; H, 6.15; N, 12.72 .

EXAMPLE 7

Dimethyl N-{5-[2-(4-hydroxy-6-pivaloylaminopyrrolo[2,3-d]pyrimidin-3-yl)ethyl]thien-2-ylcarbonyl}-L-glutamate By subjecting dimethyl N-[5-(4-hydroxy-6-pivaloylaminopyrrolo[2,3-d]pyrimidin-3-yl)ethynyl)thien-2-ylcarbonyl]-L-glutamate to the hydrogenation procedure of Example 6, there is obtained dimethyl N-{5-[2-(4-hydroxy-6-pivaloylaminopyrrolo[2,3-d]pyrimidin-3-yl)-ethyl]thien-2-ylcarbonyl}-L-glutamate.

Similarly the following compounds are subjected to the hydrogenation of Example 6:

(a) dimethyl N-[2-fluoro-4-(4-hydroxy-6-pivaloylaminopyrrolo[2,3-d]pyrimidin-3-ylethynyl)benzoyl]-L-glutamate;

(b) dimethyl N-[3-fluoro-4-(4-hydroxy-6-pivaloylaminopyrrolo[2,3-d]pyrimidin-3-ylethynyl)-benzoyl]-L-glutamate;

(c) diethyl N-[4-(4-hydroxy-6-pivaloylaminopyrrolo[2,3-d]pyrimidin-3-ylethynyl)thien-2-ylcarbonyl]-L-glutamate;

(d) diethyl N-[5-(4-hydroxy-6-pivaloylaminopyrrolo[2,3-d]pyrimidin-3-ylethynyl)thien-3-ylcarbonyl]-L-glutamate;
(e) dimethyl N-[5-(4-hydroxy-6-pivaloylaminopyrrolo[2,3-d]pyrimidin-3-yl)pent-4-ynoyl]-L-glutamate;
(f) dimethyl N-[7-(4-hydroxy-6-pivaloylaminopyrrolo[2,3-d]pyrimidin-3-yl)hept-6-enoyl]-L-glutamate;
(g) dimethyl N-[6-(4-hydroxy-6-pivaloylaminopyrrolo[2,3-d]pyrimidin-3-yl)hex-5-ynoyl]-L-glutamate;
(h) methyl 4-(4-hydroxy-6-pivaloylaminopyrrolo[2,3-d]pyrimidin-3-ylethynyl)benzoate;
(i) 3-(4-methylphenyl)ethynyl-4-hydroxy-6-pivaloylaminopyrrolo[2,3-d]pyrimidine;
(j) 3-phenylethynyl-4-hydroxy-6-pivaloylaminopyrrolo[2,3-d]pyrimidine;
(k) 3-(4-chlorophenyl)ethynyl-4-hydroxy-6-pivaloylaminopyrrolo[2,3-d]pyrimidine;
(l) 3-(4-fluorophenyl)ethynyl-4-hydroxy-6-pivaloylaminopyrrolo[2,3-d]pyrimidine;
(m) 3-(3-fluorophenyl)ethynyl-4-hydroxy-6-pivaloylaminopyrrolo[2,3-d]pyrimidine;
(n) 3-(4-methoxyphenyl)ethynyl-4-hydroxy-6-pivaloylaminopyrrolo[2,3-d]pyrimidine;
(o) methyl 4-(4-hydroxy-5-pivaloyloxy-6-methyl-pyrrolo[2,3-d]pyrimidin-3-ylethynyl)benzoate;
(p) 3-(4-methylphenyl)ethynyl-4-hydroxy-5-pivaloyloxy-6-methylpyrrolo[2,3-d]pyrimidine;
(q) 3-phenylethynyl-4-hydroxy-5-pivaloyloxy-6methylpyrrolo[2,3-d]pyrimidine;
(r) 3-(4-chlorophenyl)ethynyl-4-hydroxy-5-pivaloyloxy-6-methylpyrrolo[2,3-d]pyrimidine;
(s) 3-(4-fluorophenyl)ethynyl-4-hydroxy-5-pivaloyloxy-6-methylpyrrolo[2,3-d]pyrimidine;
(t) 3-(4-methoxyphenyl)ethynyl-4-hydroxy-5-pivaloyloxy-6-methylpyrrolo[2,3-d]pyrimidine;
(u) methyl 4-(4-hydroxypyrrolo[2,3-d]pyrimidin-3-ylethynyl)benzoate;
(v) 3-(4-methylphenyl)ethynyl-4-hydroxypyrrolo2,3-d]pyrimidine;
(w) 3-phenylethynyl-4-hydroxypyrrolo[2,3-d]pyrimidine;
(x) 3-(4-chlorophenyl)ethynyl-4-hydroxypyrrolo2,3-d]pyrimidine;
(y) 3-(4-fluorophenyl)ethynyl-4-hydroxypyrrolo2,3-d]pyrimidine; and
(z) 3-(4-methoxyphenyl)ethynyl-4-hydroxypyrrolo[2,3-d]pyrimidine.

There are respectively obtained:
(a) dimethyl N-[2-fluoro-4-(4-hydroxy-6-pivaloylaminopyrrolo[2,3-d]pyrimidin-3-ylethyl)benzoyl]-L-glutamate;
(b) dimethyl N-[3-fluoro-4-(4-hydroxy-6-pivaloylaminopyrrolo[2,3-d]pyrimidin-3-ylethyl)benzoyl]-L-glutamate;
(c) diethyl N-[4-(4-hydroxy-6-pivaloylaminopyrrolo[2,3-d]pyrimidin-3-ylethyl)thien-2-ylcarbonyl]-L-glutamate;
(d) diethyl N-[5-(4-hydroxy-6-pivaloylaminopyrrolo[2,3-d]pyrimidin-3-ylethyl)thien-3-ylcarbonyl]-L-glutamate;
(e) dimethyl N-[5-(4-hydroxy-6-pivaloylaminopyrrolo[2,3-d]pyrimidin-3-yl)pentyl]-L-glutamate;
(f) dimethyl N-[7-(4-hydroxy-6-pivaloylaminopyrrolo[2,3-d]pyrimidin-3-yl)heptyl]-L-glutamate;
(g) dimethyl N-[6-(4-hydroxy-6-pivaloylaminopyrrolo[2,3-d]pyrimidin-3-yl)hexyl]-L-glutamate;
(h) methyl 4-[2-(4-hydroxy-6-pivaloylaminopyrrolo[2,3-d]pyrimidin-3-yl)ethyl]benzoate;
(i) 3-[2-(4-methylphenyl)ethyl]-4-hydroxy-6-pivaloylaminopyrrolo[2,3-d]pyrimidine;
(j) 3-(2-phenylethyl)-4-hydroxy-6-pivaloylaminopyrrolo [2,3-d]pyrimidine;
(k) 3-[2-(4-chlorophenyl)ethyl]-4-hydroxy-6-pivaloylaminopyrrolo[2,3-d]pyrimidine;
(l) 3-[2-(4-fluorophenyl)ethyl]-4-hydroxy-6-pivaloylaminopyrrolo[2,3-d]pyrimidine;
(m) 3-[2-(3-fluorophenyl)ethyl]-4-hydroxy-6-pivaloylaminopyrrolo[2,3-d]pyrimidine;
(n) 3-[2-(4-methoxyphenyl)ethyl]-4-hydroxy-6-pivaloylaminopyrrolo[2,3-d]pyrimidine;
(o) methyl 4-[2-(4-hydroxy-6-methylpyrrolo[2,3-d]pyrimidin-3 -yl)ethyl]benzoate;
(p) 3-[2-(4-methylphenyl)ethyl]-4-hydroxy-5-pivaloyloxy-6-methylpyrrolo[2,3-d]pyrimidine;
(q) 3-(2-phenylethyl)-4-hydroxy-5-pivaloyloxy-6methylpyrrolo[2,3-d]pyrimidine;
(r) 3-[2-(4-chlorophenyl)ethyl]-4-hydroxy-5-pivaloyloxy-6-methylpyrrolo [2,3-d]pyrimidine;
(s) 3-[2-(4-fluorophenyl)ethyl]-4-hydroxy-5-pivaloyloxy-6-methylpyrrolo[2,3-d]pyrimidine;
(t) 3-[2-(4-methoxyphenyl)ethyl]-4-hydroxy-5-pivaloyloxy-6-methylpyrrolo[2,3-d]pyrimidine;
(u) methyl 4-[2-(4-hydroxypyrrolo[2,3-d]pyrimidin-3-yl)ethyl]benzoate;
(v) 3-[2-(4-methylphenyl)ethyl]-4-hydroxypyrrolo2,3-d]pyrimidine;
(w) 3-(2-phenylethyl)-4-hydroxypyrrolo[2,3 -d]pyrimidine;
(x) 3-[2-(4-chlorophenyl)ethyl]-4-hydroxypyrrolo2,3-d]pyrimidine;
(y) 3-[2-(4-fluorophenyl)ethyl]-4-hydroxypyrrolo2,3-d]pyrimidine; and
(z) 3-[2-(4-methoxyphenyl)ethyl]-4-hydroxypyrrolo2,3-d]pyrimidine.

EXAMPLE 8

Diethyl N-[4-55 1-(Tetrahydropyr-2-yloxy)-3-(4-hydroxy-6-pivaloylaminopyrrolo[2,3-d]pyrimidin-3-yl)prop-2-yl}benzoyl]glutamate A solution of 1.16 g of diethyl N-[4-(1-(tetrahydropyr-2-yloxy)-3-(4-hydroxy-6-pivaloylaminopyrrolo[2,3-d]pyrimidin-3-yl)prop-2-en-2-yl)benzoyl]glutamate and 174 mg (20%) of amorphous platinum (IV) oxide in 150 ml of glacial acetic acid is hydrogenated for 10 hours at 50 psi. The reaction mixture is diluted with 50 ml of methanol and filtered through Celite. The filtrate is concentrated and diluted with ethyl acetate. The solid which forms after cooling for 15 hour is collected by filtration, washed with cold ethyl acetate and dried to give diethyl N-[4-(1-(tetrahydropyr-2-yloxy)-3-(4-hydroxy-6-pivaloylaminopyrrolo[2,3-d]pyrimidin-3-yl)prop-2-yl)benzoyl]glutamate.

EXAMPLE 9

Dimethyl N-{4-0[2-(4-hydroxypyrrolo[2,3-d]pyrimidin-3-yl)ethyl]benzoyl}-L-glutamate A mixture of 1.1 g of dimethyl N-[4-(4-hydroxypyrrolo[2,3-d]pyrimidin-3-ylethynyl)benzoyl]-L-glutamate in 100 mL of 50% methanol in methylene chloride and 0.8 g of 3% palladium-on-carbon is hydrogenated at 50 p.s.i. for 24 hours, filtered, and concentrated under reduced pressure. Ether is added to the residue and the solid is collected by filtration and dried to yield 0.67 g of dimethyl N-{4-[2-(4-hydroxyaminopyrrolo [2,3-d]pyrimidin-3-yl)ethyl]benzoyl)-L-glutamate. mp 170°-172 °C. ¹NMR (d₆-DMSO)δ1.94–2.14 (m, 2H), 2.44 (t, J=7.4 Hz, 2H), 2.93–3.02 (m, 2H), 3.57 (s, 3H), 3.63 (s, 3H), 4.40–4.70 (m, 1H), 6.71 (s, 1H), 7.29 (d, J=8.2 Hz, 2 H), 7.77 (m, 3 H), 8.66 (d, J=7.4 Hz, 1 H), 11.52 (s, 1H), 11.71 (s, 1H).

In a similar fashion from dimethyl N-[4-(4-hydroxy-5-pivaloyloxy-6-methylpyrrolo[2,3-d]pyrimidin-3-ylethynyl)benzoyl]-L-glutamate, there is obtained according to this procedure dimethyl N-(4-[2-(4-hydroxy-5-pivaloyloxy-6-methylpyrrolo[2,3-d]pyrimidin-3-yl)ethyl]benzoyl)-L-glutamate, m.p. 163° C.

EXAMPLE 10

N-{4-[2-(4-hydroxy-6-pivaloylaminopyrrolo[2,3-d]pyrimidin-3-yl)ethyl]benzoyl}-L-glutamic Acid A mixture of 1.5 g of dimethyl N-(4-[2-(4-hydroxy6-pivaloylaminopyrrolo[2,3-d]pyrimidin-3-yl)ethyl]benzoyl)-L-glutamate in 10 mL of 1N sodium hydroxide is stirred at ambient temperatures for three days to form the sodium salt of N-(4-[2-(4-hydroxy-6-aminopyrrolo[2,3-d]pyrimidin-3-yl)ethyl]benzoyl)-L-glutamic acid. This is neutralized with glacial acetic acid. The solid which forms is collected by filtration and recrystallized from 50% methanol in methylene chloride to give 0.8 g (67%) of N-{4-[2-(4-hydroxy-6-aminopyrrolo[2,3-d]pyrimidin-3-yl)ethyl]benzoyl)-L-glutamic acid. ¹NMR (d₆-DMSO) δ 1.80–2.00 (m, 2H), 2.10–2.30 (m, 2H), 2.77–2.820 (m, 2H), 2.89–2.93 (m, 2H), 4.13–4.19 (m, 2H), 6.25 (d, J=1.3 Hz, 1H), 7.23 (d, J=8.1 Hz, 2 H), 7.69 (d, J=8.1 Hz, 2 H), 8.13 (d, J=6.7 Hz, 1 H), 10.55 (s, 1H).

EXAMPLE 11

Diethyl N-[4-{1-hydroxy-3-(4-hydroxy-6-pivaloylaminopyrrolo[2,3-d]pyrimidin-3-yl)prop-2-yl}benzoyl]glutamate The solution of 0.94 g of diethyl N-[4-(1-(tetrahydropyr-2-yloxy)-3-(4-hydroxy-6-pivaloylaminopyrrolo-[2,3-d]pyrimidin-3-yl)prop-2-yl)benzoyl]glutamate in 40 ml of 0.1N methanolic hydrogen chloride is stirred at ambient temperatures for 2 hours. The reaction mixture is neutralized with a solution of 205 mg of sodium carbonate in 10 ml of water and most of methanol removed by evaporation under reduced pressure. One hundred milliliters of methylene chloride are added and the solution is washed twice with 20 ml of water, dried over anhydrous magnesium sulfate, and concentrated. The residue is triturated with 1:2 ethyl acetate and ether, filtered, and dried to give diethyl N-[4-{1-hydroxy-3-(4-hydroxy-6-pivaloylaminopyrrolo[2,3-d]-pyrimidin-3-yl)prop-2-yl}benzoyl]glutamate.

EXAMPLE 12

N-[4-{1-hydroxy-3-(4-hydroxy-6-aminopyrrolo[2,3-d]pyrimidin-3-yl)prop-2-yl}benzoyl]glutamic Acid A solution of 0.3 g of diethyl N-[4-{1-hydroxy-3-(4-hydroxy-6-pivaloylaminopyrrolo[2,3-d]pyrimidin-3-yl)prop-2-yl}benzoyl]glutamate in 9 ml of 1N aqueous sodium hydroxide is stirred under nitrogen at ambient temperature for 72 hours. The reaction mixture is rendered slightly acidic (pH=−4) with 1N hydrochloric acid and filtered. The solid thus collected is washed with water (5 ml) and cold ethanol (5 ml) and dried to give N-[4-(1-hydroxy-3-(4-hydroxy-6-aminopyrrolo[2,3-d]-pyrimidin-3-yl)prop-2-yl)benzoyl]glutamic acid.

Similarly from dimethyl N-(2-fluoro-4-[2-(4-hydroxy-6-pivaloylaminopyrrolo[2,3-d]pyrimidin-3-yl)-ethyl]-benzoyl}-L-glutamate and dimethyl N-{3-fluoro-4-[2-(4-hydroxy-6-pivaloylaminopyrrolo[2,3-d]pyrimidin-3yl)ethyl]benzoyl)-L-glutamate there are respectively obtained according to the foregoing procedure N-(2-fluoro-4-[2-(4-hydroxy-6-aminopyrrolo[2,3-d]pyrimidin-3-yl)ethyl]benzoyl)-L-glutamic acid, m.p. 230° (foaming), 300° C (dec.) and N-{3-fluoro-4-[2-(4-hydroxy-6-aminopyrrolo[2,3-d]pyrimidin-3-yl)ethyl]benzoyl}-L-glutamic acid, m.p. >300° C. (dec.).

In an analogous fashion to the foregoing procedure, there are respectively obtained from diethyl N-{4-[2-(4-hydroxy-6-pivaloylaminopyrrolo[2,3-d]pyrimidin-3-yl)ethyl]thien-2-ylcabonyl}-L-glutamate, diethyl N-{5-[2-(4-hydroxy-6-pivaloylaminopyrrolo[2,3-d]-pyrimidin-3-yl)ethyl]thien-3-ylcabonyl}-L-glutamate, dimethyl N-{5-[2-(4-hydroxy-6-pivaloylaminopyrrolo[2,3d]pyrimidin-3-yl)ethyl]fur-2-ylcabonyl}-L-glutamate, and dimethyl N-{5-[2-(4-hydroxy-6-pivaloylaminopyrrolo[2,3-d]pyrimidin-3-yl)ethyl]thien-2-ylcabonyl}-L-glutamate, the compounds N-{4-[2-(4-hydroxy-6-aminopyrrolo[2,3-d]pyrimidin-3-yl)ethyl]-thien-2-ylcarbonyl}-L-glutamic acid, N-{5-[2-(4-hydroxy-6-aminopyrrolo[2,3d]pyrimidin-3-yl)ethyl]thien-3-ylcarbonyl)-L-glutamic acid, N-{5-[2-(4-hydroxy-6-aminopyrrolo[2,3-d]pyrimidin-3-yl)ethyl]fur-2-ylcarbonyl}-L-glutamic acid, m.p. 200°–203° C., and N-{5-[2-(4-hydroxy-6-aminopyrrolo[2,3d]pyrimidin-3-yl)ethyl]thien-2-ylcarbonyl}-L-glutamic acid, m.p. 241°–243° C.

Similarly obtained from dimethyl N-[5-(4-hydroxy6-pivaloylaminopyrrolo[2,3-d]pyrimidin-3-yl)pentanoyl]-L-glutamate, dimethyl N-[7-(4-hydroxy-6-pivaloylaminopyrrolo[2,3-d]pyrimidin-3-yl)heptanoyl]-L-glutamate, and dimethyl N-[6-(4-hydroxy-6-pivaloylaminopyrrolo[2,3-d]pyrimidin-3-yl)-hexanoyl]-L-glutamate, are, respectively, N-[5-(4-hydroxy-6-aminopyrrolo[2,3-d]pyrimidin-3-yl)pentanoyl]-L-glutamic acid, N-[7-(4-hydroxy-6-aminopyrrolo[2,3-d]pyrimidin-3-yl)heptanoyl]-L-glutamic acid, and N-[6-(4-hydroxy-6-aminopyrrolo[2,3-d]-pyrimidin-3-yl)hexanoyl]-L-glutamic acid.

EXAMPLE 13

N-{4-[2-(4-hydroxypyrrolo[2,3-d]pyrimidin-3-yl)ethyl]-benzoyl}-L-glutamic Acid

A mixture of 0.5 g of dimethyl N-{4-[2-(4hydroxypyrrolo[2,3-d]pyrimidin-3-yl)ethyl]benzoyl}-L-glutamate in 3 mL of 1N sodium hydroxide is stirred at ambient temperatures for three days to form the sodium salt of N-{4-[2-(4-hydroxy-6-aminopyrrolo[2,3-d]pyrimidin-3-yl)ethyl]benzoyl}-L-glutamic acid. This is neutralized with hydrochloric acid. The solid which forms is collected by filtration and recrystallized from methanol by addition of water to give 0.35 g (75%) of N-{4-[2-(4-hydroxypyrrolo[2,3-d]pyrimidin-3-yl)ethyl]-benzoyl}-L-glutamic acid. m.p. >230° C., ¹NMR (d₆-DMSO)δ1.-88–2.12 (m, 2H), 2.33 (t, J=7.3 Hz, 2H), 2.97 (m, 4H), 4.33–4.40 (m, 1H), 6.70 (d, J=1.2 Hz, 1H), 7.28 (d, J=7.0 Hz, 2 H), 7.76 (m, 3H), 8.50 (d, J=7.6 Hz, 1H), 11.48 (s, 1H), 11.67 (s, 1H), 12.40 (br, 1H).

In a similar fashion from dimethyl N-{4-[2-(4-hydroxy-5-pivaloyloxy-6-methylpyrrolo[2,3-d]pyrimidin-3-yl)ethyl]benzoyl}-L-glutamate, there is obtained according to the foregoing procedure first the sodium salt of N-{4-[2-(4-hydroxy-6-methylpyrrolo[2,3-d]pyrimidin-3-yl)ethyl]benzoyl}-L-glutamic acid which upon neutralization with glacial acetic acid yields N-{4-[2-(4-hydroxy-6-methylpyrrolo[2,3-d]pyrimidin-3-yl)ethyl]benzoyl}-L-glutamic acid, m.p. 291 ° C. $^1$NMR (d$_6$-DMSO)δ2.32 (m, 4H), 2.48 (s, 3H), 2.96 (m, 4H), 4.26 (m, 1H), 6.60 (s, 1H), 7.26 (d, J=8.0 Hz, 1 H), 7.75 (d, J=7.76 Hz, 1H), 8.44 (d, J=2.96 Hz, 1H), 11.26 (s, 1H), 11.59 (s, 1H) .

By subjecting methyl 4-[2-(4-hydroxy-5-pivaloyloxy-6-methylpyrrolo[2,3-d]pyrimidin-3-yl)ethyl]benzoate; 3-[2-(4-methylphenyl)ethyl]-4-hydroxy-6-pivaloylaminopyrrolo[2,3-d]pyrimidine; 3-(2-phenylethyl)4-hydroxy-6-pivaloylaminopyrrolo[2,3-d]pyrimidine; 3-[2-(4-chlorophenyl)ethyl]-4-hydroxy-6-pivaloylaminopyrrolo[2,3-d]pyrimidine; 3-[2-(4-fluorophenyl)ethyl]4-hydroxy-6-pivaloylaminopyrrolo[2,3-d]pyrimidine; 3-[2-(3-fluorophenyl)ethyl]-4-hydroxy-6-pivaloylaminopyrrolo[2,3-d]pyrimidine; 3-[2-(4-methoxyphenyl)ethyl]-4-hydroxy-6-pivaloylaminopyrrolo[2,3-d]pyrimidine; and methyl 4-[2-(4-hydroxy-6-pivaloylaminopyrrolo[2,3-d]-pyrimidin-3-yl)ethyl]benzoate to the foregoing procedure, there are respectively obtained 4-[2-(4-hydroxy-6-methylpyrrolo[2,3-d]pyrimidin-3-yl)ethyl]benzoic acid; 3-[2-(4-methylphenyl)ethyl]-4-hydroxy-6aminopyrrolo[2,3-d]pyrimidine; 3-(2-phenylethyl)-4-hydroxy-6-aminopyrrolo[2,3-d]pyrimidine; 3-[2-(4chlorophenyl)ethyl]-4-hydroxy-6-aminopyrrolo[2,3-d]pyrimidine; 3-[2-(4-fluorophenyl)ethyl]-4-hydroxy-6aminopyrrolo[2,3-d]pyrimidine; 3-[2-(3-fluorophenyl)ethyl]-4-hydroxy-6-aminopyrrolo[2,3-d]pyrimidine, m.p. 295°-298°; 3-[2-(4-methoxyphenyl)ethyl]-4-hydroxy-6aminopyrrolo[2,3-d]pyrimidine, m.p. 280°-284° C.; and 4 [2-(4-hydroxy-6-aminopyrrolo[2,3-d]pyrimidin-3-yl)ethyl]benzoic acid, m.p. >300° C.

EXAMPLE 14

Representative inhibition values against CCRF-CEM 5 cell cultures for typical compounds are as follows:

| Compound | IC$_{50}$ (μg/ml) |
|---|---|
| 4-[2-(4-hydroxy-6-amino-pyrrolo[2,3-d]pyrimidin-3-yl)-ethyl]benzoic acid | >20.00 |
| N-{4-[2-(4-hydroxy-6-amino-pyrrolo[2,3-d]pyrimidin-3-yl)-ethyl]benzoyl}-L-glutamic acid | 0.004 |
| 3-[2-(4-methoxyphenyl)ethyl]-4-hydroxy-6-aminopyrrolo[2,3-d]pyrimidine | >20.00 |
| N-{2-fluoro-4-[2-(4-hydroxy-6-aminopyrrolo[2,3-d]pyrimidin-3-yl)ethyl]benzoyl}-L-glutamic acid | 0.008 |
| N-{3-fluoro-4-[2-(4-hydroxy-6-aminopyrrolo[2,3-d]pyrimidin-3-yl)ethyl]benzoyl}-L-glutamic acid | 0.019 |
| 3-[2-(3-fluorophenyl)ethyl]-4-hydroxy-6-aminopyrrolo[2,3-d]pyrimidine | >20.00 |
| N-{5-[2-(4-hydroxy-6-amino-pyrrolo[2,3-d]pyrimidin-3-yl)ethyl]-thien-2-ylcarbonyl}-L-glutamic acid | 0.025 |
| N-{5-[2-(4-hydroxy-6-amino pyrrolo[2,3-d]pyrimidin-3-yl)ethyl] fur-2-ylcarbonyl}-L-glutamic acid | >20.00 |
| N-{4-[2-(4-hydroxy-6-methyl-pyrrolo[2,3-d]pyrimidin-3-yl)ethyl]-benzoyl}-L-glutamic acid | 0.0084 |
| N-{4-[2-(4-hydroxypyrrolo[2,3-d]pyrimidin-3-yl)ethyl]benzoyl}-L-glutamic acid | 1.20 |

The cytotoxicity of these compounds is not reversed by the addition of hypoxanthine or AICA, suggesting they do not inhibit the purine de novo biosynthesis pathway, but is reversed by thymidine, indicating thymidylate synthetase is the main target. Cytotoxicity is also reversed by addition of leucovorin, indicating the cytotoxicity is due to antagonism of a folate-related mechanism.

In vivo activity can be seen from the following representative data for N-{4-[2-(4-hydroxy-6-aminopyrrolo[2,3-d]pyrimidin-3-yl)ethyl]benzoyl}-L-glutamic acid against the L5178Y/TK$^-$ tumor line in DBA/2 mice (female), administration being ip in a total volume of 0.5 mL daily for eight days:

| | Dose % | Inhibition | Toxicity | Tumor Weight |
|---|---|---|---|---|
| Control | 0.0 | 0 | 0/6 | 3606 ± 2099 |
| Control | 0.0 | 0 | 0/6 | 5533 ± 1234 |
| | 200.00 | 100 | 0/7 | 0 ± 0 |
| | 100.00 | 100 | 0/7 | 0 ± 0 |
| | 50.00 | 100 | 0/6 | 0 ± 0 |
| | 25.00 | 100 | 0/7 | 0 ± 0 |
| | 12.50 | 98 | 0/7 | 102 ± 166 |

What is claimed is:

1. A compound of the formula:

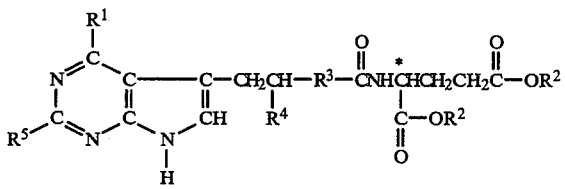

in which:

R$^1$ is —OH or —NH$_2$;

R$^2$ is hydrogen or a pharmaceutically acceptable cation:

R$^3$ is 1,4-phenylene unsubstituted or substituted with chloro, fluoro, methyl, methoxy, or trifluoromethyl;

R$^4$ is hydrogen, or methyl;

R$^5$ is amino; and the configuration about the carbon atom designated * is S.

2. A compound according to claim 1 wherein R$^1$ is —OH; R$^3$ is 1,4-phenylene, and R$^4$ is hydrogen.

3. The compound according to claim 1 which is N-{4-[2-(4-hydroxy-6-aminopyrrolo[2,3-d]pyrimidin-3-yl)ethyl]benzoyl}-L-glutamic acid.

4. The compound according to claim 1 which is N-{4-[1-hydroxy-3-(4-hydroxy-6-aminopyrrolo[2,3-d]pyrimidin-3-yl)prop-2-yl]benzoyl}glutamic acid.

5. The compound according to claim 1 which is N-{2-fluoro-4-[2-(4-hydroxy-6-aminopyrrolo[2,3-d]pyrimidin-3-yl)ethyl]benzoyl}-L-glutamic acid.

6. The compound according to claim 1 which is N-{3-fluoro-4-[2-(4-hydroxy-6-aminopyrrolo[2,3-d]pyrimidin-3-yl)ethyl]benzoyl}-L-glutamic acid.

7. A compound of the formula:

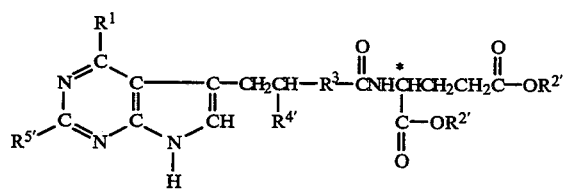

in which:

$R^1$ is —OH or —NH$_2$;

$R^{2'}$ is hydrogen, a pharmaceutically acceptable cation, or a carboxy protecting group:

$R^3$ is 1,4-phenylene unsubstituted or substituted with chloro, fluoro, methyl, methoxy, or trifluoromethyl;

$R^{4'}$ is hydrogen, or methyl;

$R^{5'}$ is amino or amino substituted with an amino protecting group; and the configuration about the carbon atom designated * is S.

* * * * *